United States Patent
Clack-Hopkins

(10) Patent No.: US 7,959,122 B1
(45) Date of Patent: Jun. 14, 2011

(54) CATHETER DRAINAGE BAG HOLDING ASSEMBLY

(76) Inventor: Wanda L. Clack-Hopkins, Maple Heights, OH (US)

( * ) Notice: Subject to any disclaimer, the term of this patent is extended or adjusted under 35 U.S.C. 154(b) by 246 days.

(21) Appl. No.: 12/252,389

(22) Filed: Oct. 16, 2008

(51) Int. Cl.
*A47G 1/10* (2006.01)

(52) U.S. Cl. .................. 248/316.7; 248/315; 211/107

(58) Field of Classification Search ............... 248/316.7, 248/231.81, 230.7, 229.16, 690, 74.2, 315; 24/546, 455, 17 A, 17 B, 22, 486, 135 N; D8/394; 211/41.9, 107, 205
See application file for complete search history.

(56) References Cited

U.S. PATENT DOCUMENTS

| | | | | |
|---|---|---|---|---|
| 560,447 A | * | 5/1896 | Voege | 211/107 |
| 582,086 A | * | 5/1897 | Poole | 211/22 |
| 1,207,916 A | * | 12/1916 | Hendricks | 248/231.71 |
| 1,975,303 A | * | 10/1934 | Walker et al. | 248/125.1 |
| 2,559,739 A | * | 7/1951 | Sherman | 211/70 |
| 2,689,995 A | * | 9/1954 | Smith | 285/61 |
| 2,723,431 A | * | 11/1955 | Di Renzo | 24/301 |
| 3,893,813 A | * | 7/1975 | Johnson | 422/104 |
| 4,211,380 A | * | 7/1980 | Lillegard et al. | 248/229.15 |
| 4,757,641 A | * | 7/1988 | Penrod | 47/39 |
| 4,832,294 A | | 5/1989 | Eidem | |
| 5,005,793 A | | 4/1991 | Shillington | |
| 5,114,023 A | | 5/1992 | Lavin | |
| 5,320,312 A | * | 6/1994 | Hoenninger | 248/68.1 |
| 5,322,253 A | | 6/1994 | Stevens | |
| D391,636 S | | 3/1998 | Zwerk | |
| 6,499,704 B2 | | 12/2002 | Oddsen, Jr. | |
| 6,969,031 B2 | | 11/2005 | Ugent et al. | |
| 2002/0096608 A1 | | 7/2002 | Cedarberg, III | |

* cited by examiner

Primary Examiner — A. Joseph Wujciak, III

(57) ABSTRACT

A catheter drainage bag holding assembly includes a clamp with an arcuate member having a pair of free ends. The arcuate member forms at least 60% of a complete circle. A threaded rod is threadably coupled to and extends through the arcuate member. The arcuate member is positionable on a post and the rod is abuttable against the post. A leg is attached to and extends away from the arcuate member. A primary loop is attached to the leg. The primary loop lies in same plane as the arcuate member. At least one of hook from a catheter drainage bag is extendable into the primary hook.

6 Claims, 6 Drawing Sheets

CATHETER DRAINAGE BAG HOLDING ASSEMBLY

BACKGROUND OF THE INVENTION

Field of the Invention

The present invention relates to catheter bag holding devices and more particularly pertains to a new catheter bag holding device for holding a urinary catheter drainage bag to a vertical post to allow for better movement of a patient with an implanted urinary catheter.

SUMMARY OF THE INVENTION

The present invention meets the needs presented above by generally comprising a clamp that includes an arcuate member having a pair of free ends. The arcuate member forms at least 60% of a complete circle. A threaded rod is threadably coupled to and extends through the arcuate member. The arcuate member is positionable on a post and the rod is abuttable against the post. A leg is attached to and extends away from the arcuate member. A primary loop is attached to the leg. The primary loop lies in same plane as the arcuate member. At least one of hook from a catheter drainage bag is extendable into the primary hook.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

The objects of the invention, along with the various features of novelty which characterize the invention, are pointed out with particularity in the claims annexed to and forming a part of this disclosure.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
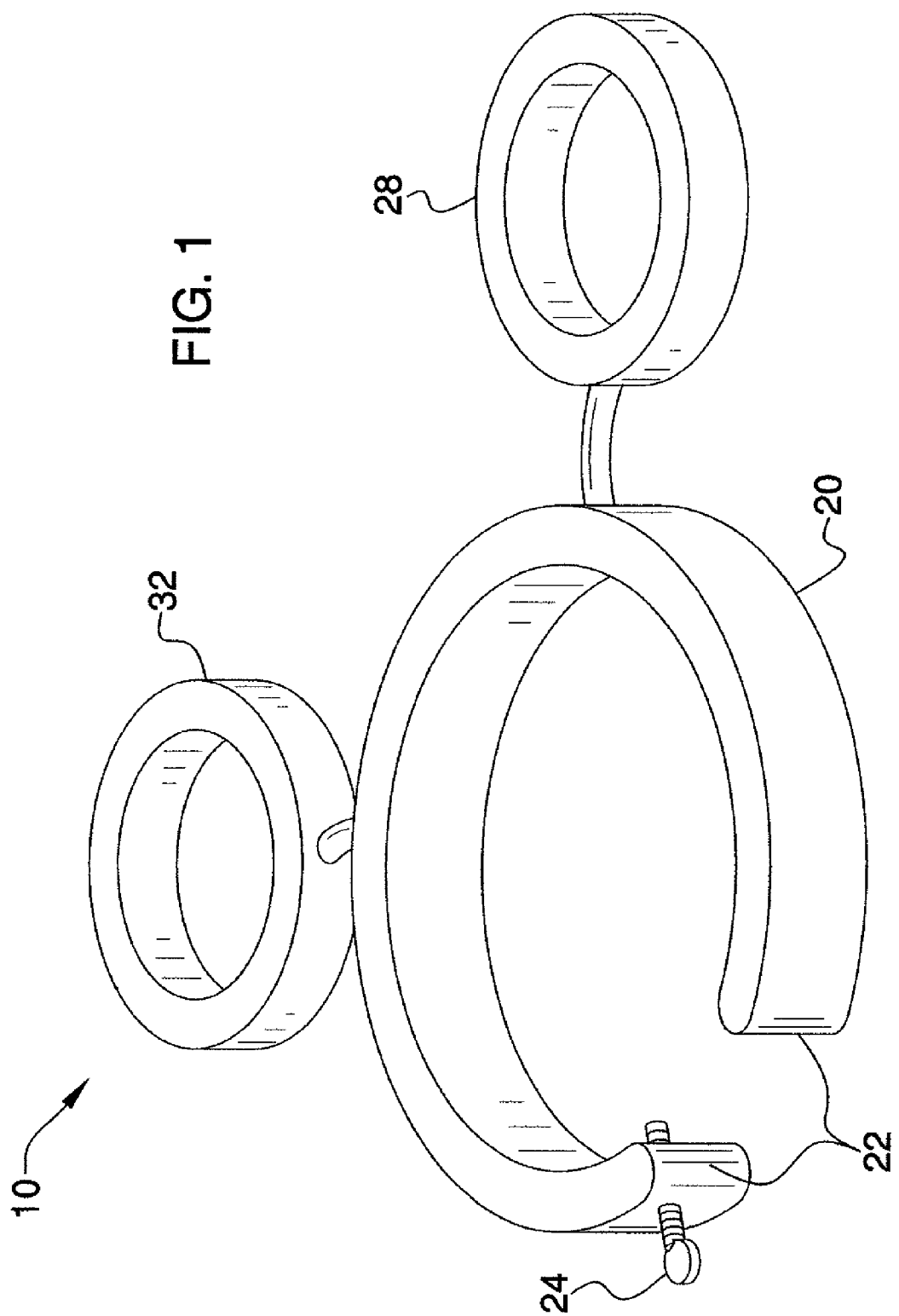
FIG. 1 is a top perspective view of a catheter drainage bag holding assembly according to the present invention.
Figure 2:
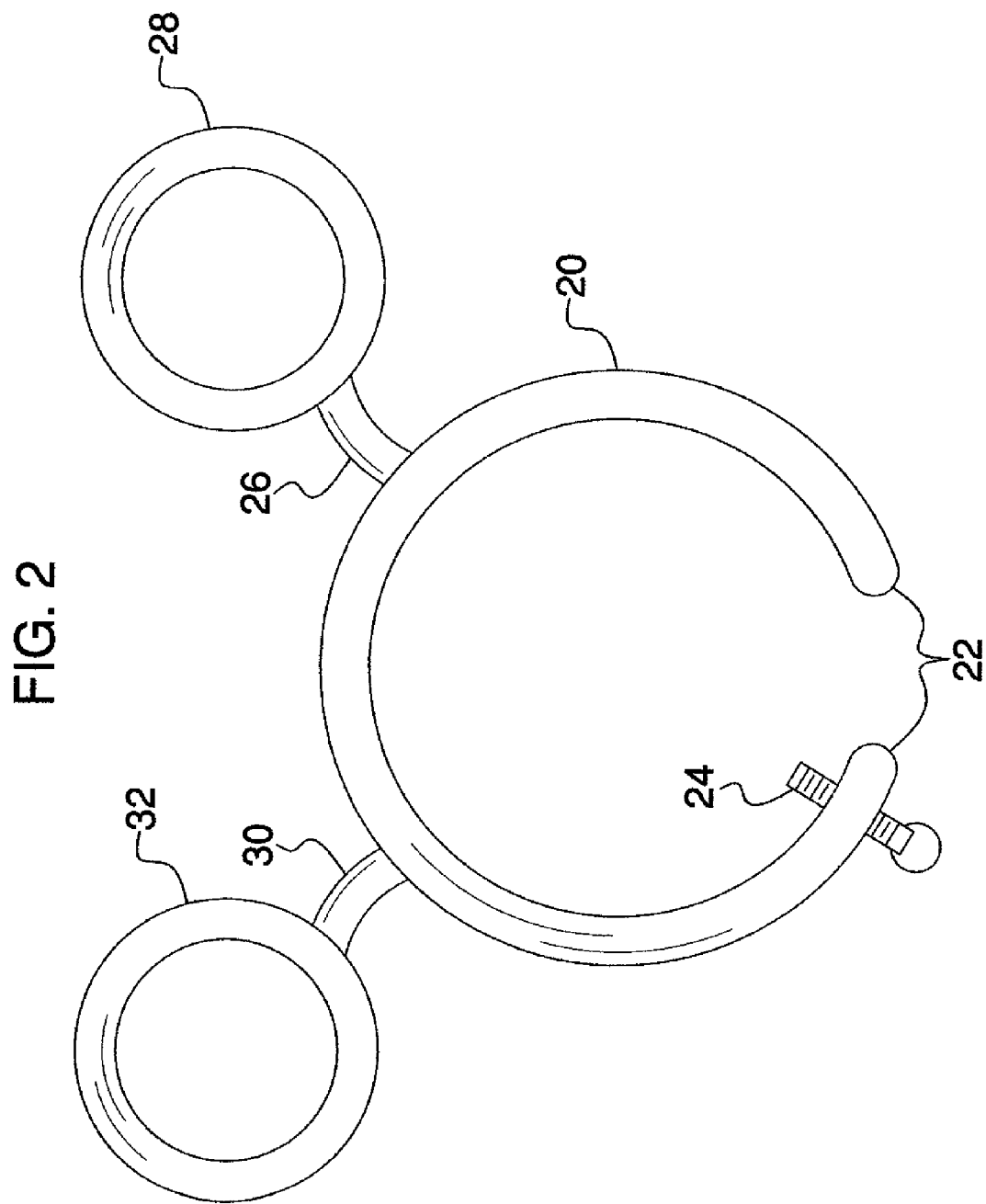
FIG. 2 is a top view of the present invention.
Figure 3:
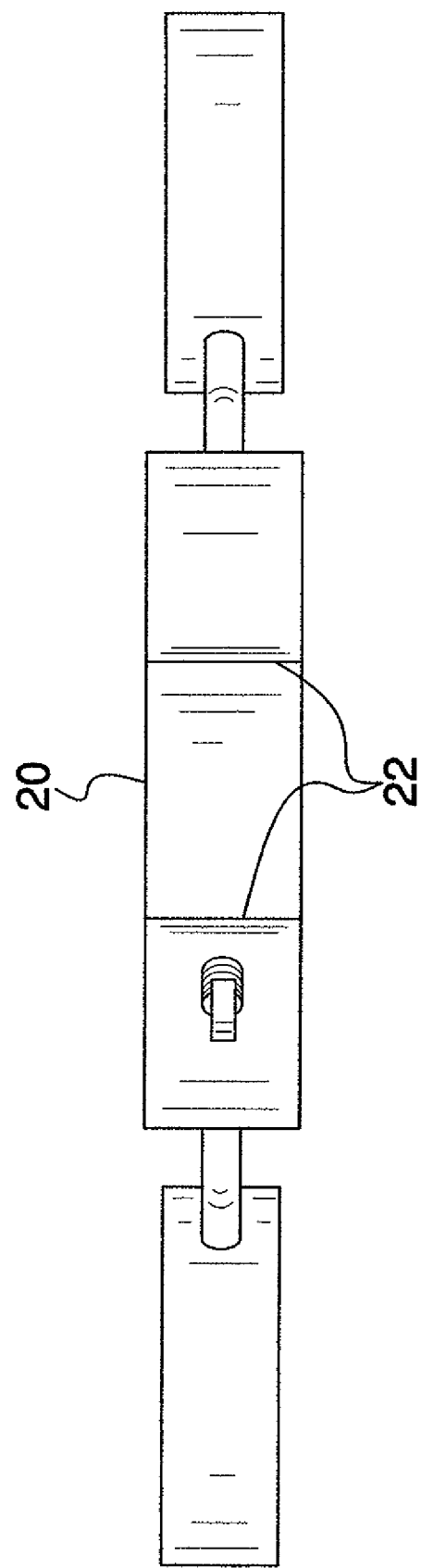
FIG. 3 is a front view of the present invention.
Figure 4:
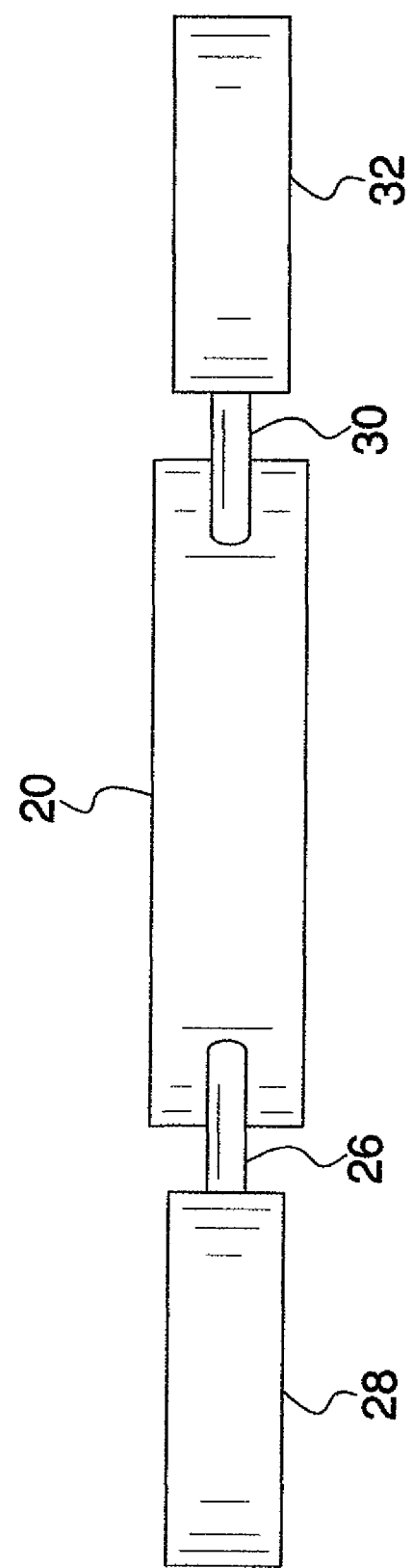
FIG. 4 is a back view of the present invention.
Figure 5:
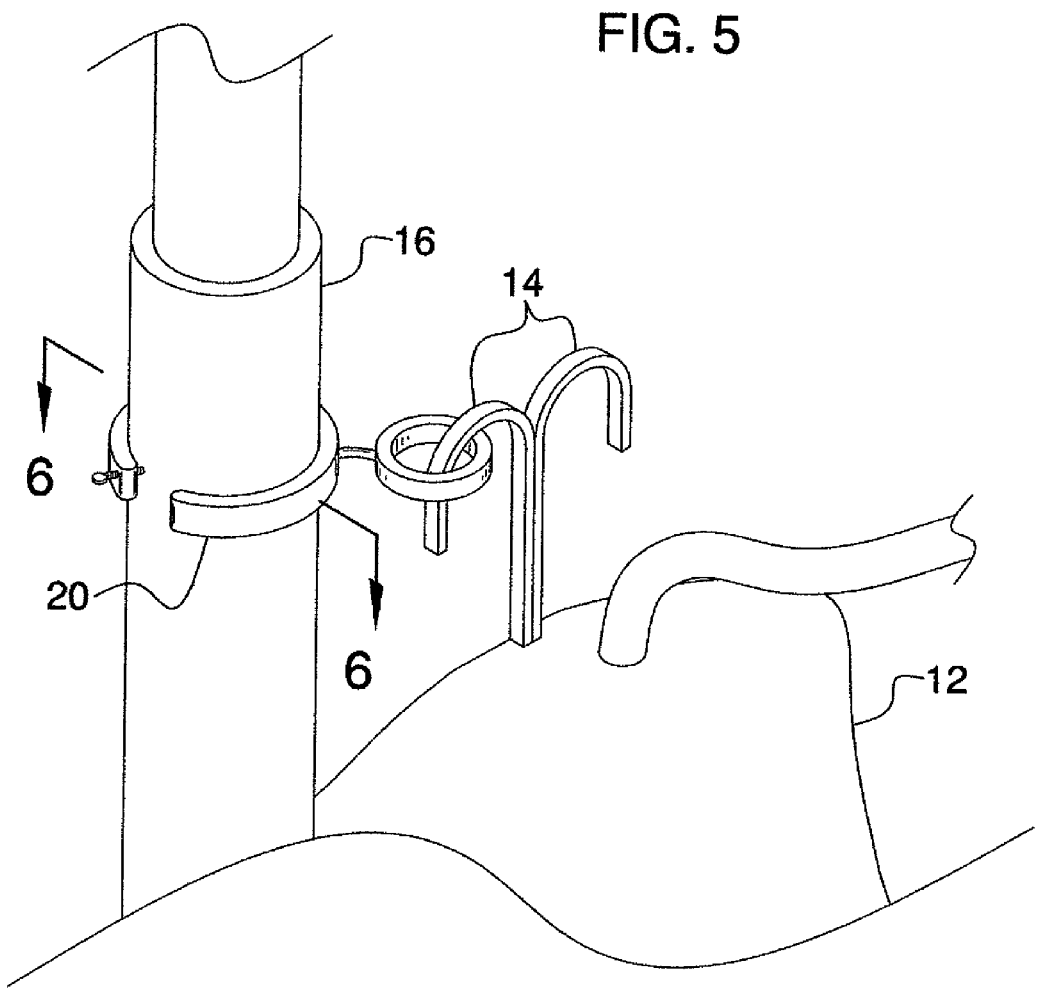
FIG. 5 is a perspective in-use view of the present invention.
Figure 6:
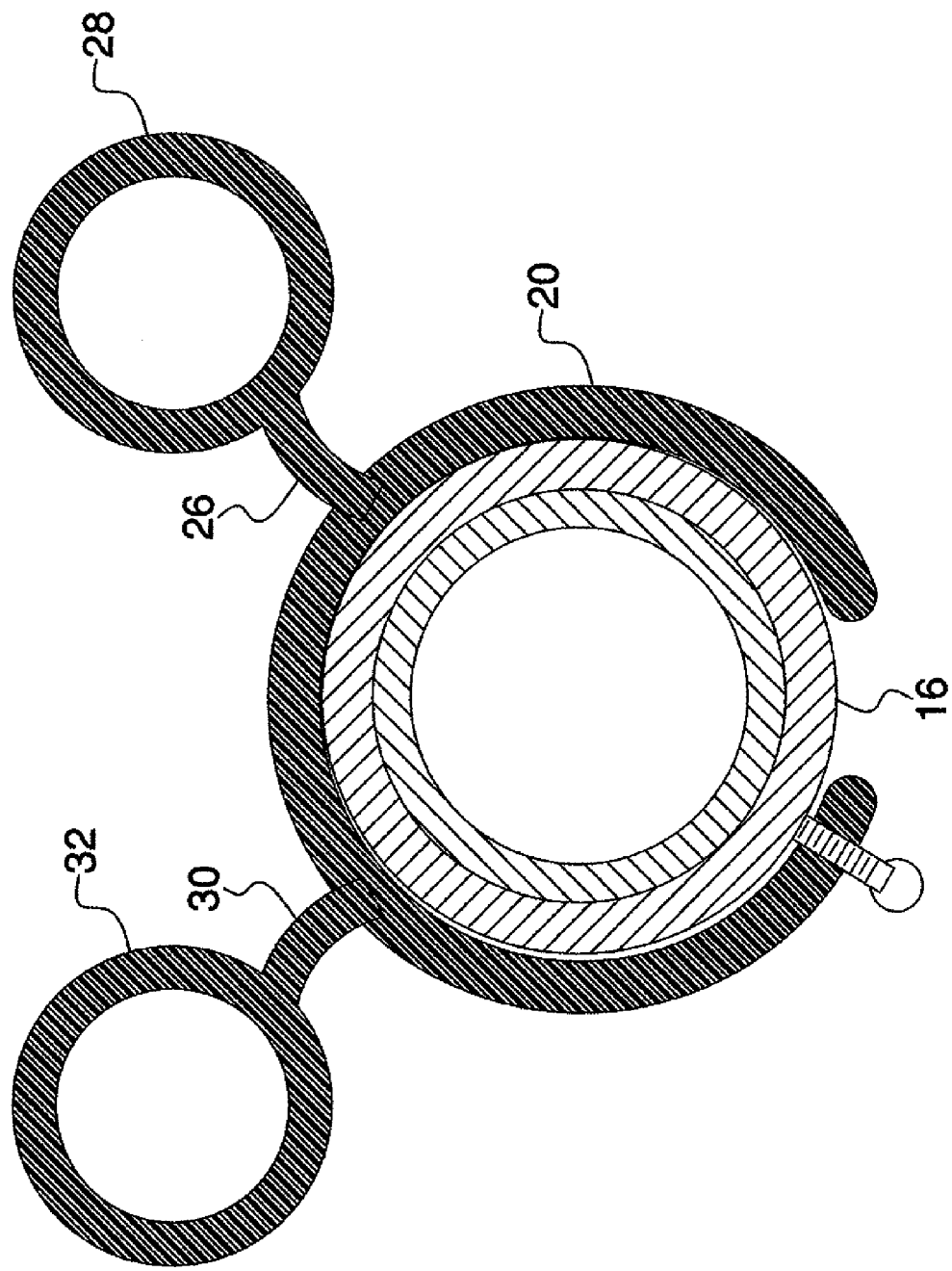
FIG. 6 is a cross-sectional view taken along line 6-6 of FIG. 5 of the present invention.

With reference now to the drawings, and in particular to FIGS. 1 through 6 thereof, a new catheter bag holding device embodying the principles and concepts of the present invention and generally designated by the reference numeral 10 will be described.

As best illustrated in FIGS. 1 through 6, the catheter drainage bag holding assembly 10 is typically to be used with a urinary catheter drainage bag 12 of the type having a pair of hooks 14 attached thereto and known as Foley catheter bags. The assembly 10 is positionable on a vertical post 16 which generally will have a bottom end, not shown, including a plurality of wheels for moving the post 16. The assembly 10 generally comprises a clamp 20 that includes an arcuate member having a pair of free ends 22. The arcuate member 20 forms at least 60% of a complete circle and a space between the free ends 22 allows the clamp 20 to be positioned on the post 16, though a top end of the post 16 may be extended through the clamp 20 as well. A threaded rod 24 is threadably coupled to and extends through the arcuate member 20. The arcuate member 20 is positionable on the post and the rod 24 is abuttable against the post 16 to frictionally couple the arcuate member 20 to the post 16. The arcuate member 20 has a greatest internal width equal to 1½ inches.

A leg 26 is attached to and extends away from the arcuate member 20. The leg 26 has a length less than 3 inches. A primary loop 28 is attached to the leg 26 and lies in same plane as the arcuate member 20. An arm 30 is attached to and extends away from the arcuate member 20 and has a length less than 3 inches. A secondary loop 32 is attached to the arm 30. The secondary loop 32 lies in a same plane as the arcuate member 20 and the primary loop 28. Each of the primary 28 and secondary 32 loops has an internal diameter between ½ inch and 1½ inches, and more particularly between ½ inch and 1 inch. The secondary 32 and primary 28 loops are spaced from each other less than 2 inches.

In use, at least one of the hooks 14 is extendable into the primary hook 28. This allows a patient, using a catheter drainage bag 12, to walk with the bag 12 without fear of bag leakage. Typically such bags are attached to the patient's leg and they can fall off, be uncomfortable to wear or the tubes may come apart causing a leak due to the movement of the patient's legs. As can be appreciated, both of the primary 28 and secondary 32 loops may each receive one of the hooks 14 to further secure the bag 12 to the post 16.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A urinary catheter drainage bag holding assembly to releasably secure a catheter drainage bag having hooks thereon to a vertical post, said assembly comprising:

a clamp including an arcuate member having a pair of free ends, said arcuate member forming at least 60% of a complete circle, a threaded rod being threadably coupled to and extending through said arcuate member, said arcuate member being positionable on the post and said rod being abuttable against the post;

a leg being attached to and extending away from said arcuate member;

a primary loop being attached to said leg, said primary loop lying in same plane as said arcuate member;

wherein at least one of the hooks is extendable into said primary loop;

an arm being attached to and extending away from said arcuate member; and a secondary loop being attached to said arm, said secondary loop lying in a same plane as said arcuate member and said primary loop.

2. The assembly according to claim 1, wherein said arcuate member having a greatest internal width equal to 1½ inches.

3. The assembly according to claim 1, where said leg has a length less than 3 inches.

4. The assembly according to claim 3, wherein said primary loop has a diameter between ½ inch and 1½ inches.

5. The assembly according to claim 1, wherein said secondary and primary loops are spaced from each other less than 2 inches.

6. A urinary catheter drainage bag holding assembly to releasably secure a catheter drainage bag having hooks thereon to a vertical post, said assembly comprising:

a clamp including an arcuate member having a pair of free ends, said arcuate member forming at least 60% of a complete circle, a threaded rod being threadably coupled to and extending through said arcuate member, said arcuate member being positionable on the post and said rod being abuttable against the post, said arcuate member having a greatest internal width equal to 1½ inches;

a leg being attached to and extending away from said arcuate member, said leg having a length less than 3 inches;

a primary loop being attached to said leg, said primary loop lying in same plane as said arcuate member;

an arm being attached to and extending away from said arcuate member, said arm having a length less than 3 inches;

a secondary loop being attached to said arm, said secondary loop lying in a same plane as said arcuate member and said primary loop, each of said primary and secondary loops having an internal diameter between ½ inch and 1½ inches, said secondary and primary loops being spaced from each other less than 2 inches; and wherein at least one of the hooks is extendable into said primary loop.

* * * * *